(12) United States Patent (10) Patent No.: US 9,108,985 B2
Karch et al. (45) Date of Patent: Aug. 18, 2015

(54) PROCESS FOR PREPARING TRIALKYLGALLIUM COMPOUNDS

(71) Applicant: Umicore AG & CO. KG, Hanau (DE)

(72) Inventors: Ralf Karch, Kleinostheim (DE); Andreas Rivas-Nass, Schriesheim (DE); Annika Frey, Hanau (DE); Tobias Burkert, Murr (DE); Eileen Woerner, Nidderau (DE); Angelino Doppiu, Seligenstadt (DE)

(73) Assignee: UMICORE AG & CO, KG, Hanau-Wolfgang (DE)

( * ) Notice: Subject to any disclaimer, the term of this patent is extended or adjusted under 35 U.S.C. 154(b) by 0 days.

(21) Appl. No.: 13/261,859

(22) PCT Filed: Nov. 28, 2012

(86) PCT No.: PCT/EP2012/073772
§ 371 (c)(1),
(2) Date: May 14, 2014

(87) PCT Pub. No.: WO2013/083450
PCT Pub. Date: Jun. 13, 2013

(65) Prior Publication Data
US 2014/0256974 A1    Sep. 11, 2014

(30) Foreign Application Priority Data
Nov. 28, 2011 (DE) .......................... 10 2011 119 487
Jul. 16, 2012 (DE) .......................... 10 2012 013 941

(51) Int. Cl.
*C07F 5/00* (2006.01)
*C23C 16/30* (2006.01)
*C23C 16/18* (2006.01)

(52) U.S. Cl.
CPC . *C07F 5/00* (2013.01); *C23C 16/18* (2013.01); *C23C 16/301* (2013.01)

(58) Field of Classification Search
CPC ....................................................... C07F 5/00
USPC ............................................................ 556/1
See application file for complete search history.

(56) References Cited

U.S. PATENT DOCUMENTS 3,318,931 A    5/1967   Dützer et al.
5,043,462 A    8/1991   Sundermeyer et al.
(Continued)

FOREIGN PATENT DOCUMENTS

CN    1872861 A    12/2006
CN    1872862 A    12/2006
(Continued)

OTHER PUBLICATIONS

Gaines et al., "*Trimethylgallium*", Inorganic Syntheses, pp. 203-207.
(Continued)

*Primary Examiner* — Porfirio Nazario Gonzalez
(74) *Attorney, Agent, or Firm* — Smith, Gambrell & Russell, LLP (57) ABSTRACT

The invention relates to a process for preparing trialkylgallium compounds of the general formula $R_3Ga$. The process is based on the reaction of gallium trichloride (GaCl), optionally in a mixture with partially alkylated products, with an alkylaluminium compound of the type $R_aAlCl_b$ (where $R=C_1$-$C_5$-alkyl, $a=1$, 2 or 3, $b=0$, 1 or 2 and $a+b=3$) in the presence of at least two alkali metal halides (e.g. NaCl and KCl) as auxiliary base. Preference is given to using alkylaluminium sesquichloride ($R_3Al_2Cl_3$) or trialkylaluminium ($R_3Al$). The reaction mixture is heated to a temperature in the range from 120° C. to 250° C. and the trialkylgallium compound formed is separated off via a separator which is operated at a temperature which is more than 30° C. below the boiling point of the most volatile partially alkylated product. Complete alkylation is achieved here and partially alkylated products are recirculated to the reaction mixture. In a further step, the reaction mixture can be heated to a maximum of 350° C. and the remaining fully alkylated and partially alkylated products can be separated off. The process provides a high yield of trialkylgallium compound and displays high gallium utilization; the products are used, e.g., as precursors for MOCVD processes.

34 Claims, 1 Drawing Sheet

(56) References Cited

U.S. PATENT DOCUMENTS

| | | |
|---|---|---|
| 5,350,869 A | 9/1994 | Kanjolia et al. |
| 5,756,786 A | 5/1998 | Power et al. |
| 7,166,734 B2 | 1/2007 | Shenai-Khatkhate et al. |
| 2003/0191333 A1 | 10/2003 | Shenai-Khatkhate et al. |
| 2006/0047132 A1 | 3/2006 | Shenai-Khatkhate et al. |
| 2006/0075959 A1 | 4/2006 | Matsubara et al. |
| 2009/0149008 A1 | 6/2009 | Kryliouk et al. |

FOREIGN PATENT DOCUMENTS

| | | |
|---|---|---|
| DE | 1158977 B | 12/1963 |
| DE | 40 05 726 A1 | 10/1990 |
| EP | 1489085 A1 | 12/2004 |
| EP | 1 643 547 A1 | 4/2006 |
| EP | 1 705 719 A1 | 9/2006 |
| JP | 2006-265168 A | 10/2006 |
| JP | 2006-342101 A | 12/2006 |
| JP | 2009-126835 A | 6/2009 |
| JP | 2010-195690 A | 9/2010 |
| WO | 00/37475 A1 | 6/2000 |
| WO | 02/07848 A1 | 1/2002 |
| WO | 2013/083449 A1 | 6/2013 |

OTHER PUBLICATIONS

J.J. Eisch et al, "Organometallic Compounds of Group III. I. The Preparation of Gallium and Indium Alkyls form Organoaluminum Compounds[1a]", vol. 84; No. 19, pp. 3605-3610, Oct. 17, 1962.

Starowieyski et al., "Synthesis and purification of MOCVD: molecular structure of $(KF)_4 4\ (Me_3Ga)$", Applied organometallic Chemistry, vol. 14, pp. 616-622, 2000.

Notification of Transmittal of the International Search Report and The Written Opinion for Application No. PCT/EP2012/073772 mailed Mar. 25, 2013.

C. A. Kraus et al., "Trimethyl Gallium, Trimethyl Gallium Etherate and Trimethyl Gallium Ammine", Chemistry: Kraus and Toonder, Proc. N.A.S.; 1933; pp. 292-298.

D. F. Foster et al., "7. Electronic Grade Alkyls of Group 12 and 13 Elements"; Inorganic Syntheses, vol. 31, 1997, pp. 29-66.

L. I. Zakharkin et al,. "A Simple Synthesis of Non-Solvated Trimethylgallium and Triethylgallium"; Synth. React. Inorg. Met.-Org., and Nano-Met. Chem. vol. 29(7); (1999) 1243-1247.

Gaines et al., "Trimethylgallium,", Inorganic Syntheses, vol. 15, 1974, pp. 203-207.

PROCESS FOR PREPARING TRIALKYLGALLIUM COMPOUNDS

INTRODUCTION

The invention relates to a process for the inexpensive and environmentally friendly preparation of trialkyl compounds of gallium. The compounds have the general formula $$R_3Ga$$

where R is a $C_1$-$C_5$-alkyl group, preferably methyl or ethyl.

The process is based in principle on the reaction of gallium trichloride ($GaCl_3$) with alkylaluminium compounds of the type $R_aAlCl_b$ (where R is a $C_1$-$C_5$-alkyl group, a=1, 2 or 3, b=0, 1 or 2 and the sum a+b=3) in the presence of at least two alkali metal halides as auxiliary base in a one-pot process. Gallium trichloride ($GaCl_3$) can optionally be present in a mixture with partially alkylated products of the type $R_cGaCl_d$ (where c, d=1 or 2 and c+d=3).

The alkylaluminium compounds of the type $R_aAlCl_b$ also encompass the alkylaluminium sesquichlorides of the formula ($R_3Al_2Cl_3$) which can be considered to be a mixture of the compounds $R_2AlCl$ and $RAlCl_2$. In particular, the methylaluminium and ethylaluminium sesquichlorides of the formulae $Me_3Al_2Cl_3$ and $Et_3Al_2Cl_3$, in which a 1:1 mixture of $Me_2AlCl$ and $MeAlCl_2$ or $Et_2AlCl$ and $EtAlCl_2$ is present, are included.

The reaction mixture is heated to a defined temperature and the trialkylgallium compound is separated off from the reaction mixture via a separator, with the partially alkylated products $R_cGaCl_d$ being able to be simultaneously recirculated to the reaction mixture. In a further stage, the reaction mixture can be heated to a maximum of 350° C. and the remaining alkylated ($R_3Ga$) and partially alkylated products ($R_cGaCl_d$) can be separated off. These compounds can be recycled and used as starting materials in a further batch, so that high gallium utilization is ensured by the process of the invention.

The present invention makes a more rapid process possible, for example in the preparation of trimethylgallium. The targetted use of inexpensive starting materials (for example methylaluminium sesquichloride) enables the process to be carried out inexpensively on an industrial scale, too. Furthermore, the yields are significantly improved.

The trialkyl compounds of the type $R_3Ga$, in particular trimethylgallium and triethylgallium, prepared according to the invention are suitable as precursors for metal organic chemical vapour deposition (MOCVD), a process which is widespread in, for example, the semiconductor and microelectronics industry.

Various processes for preparing trialkyl compounds of the type $R_3Ga$ are known in the prior art. The reaction of gallium with dimethylmercury or diethylmercury is known. However, owing to the thermal instability of the higher mercury alkyls, the high toxicity of the mercury dialkyls and the extraordinarily slow reaction, this process is unsuitable for industrial use.

Furthermore, the preparation can be effected by reaction of gallium trichloride with zinc dialkyls. However, the high light sensitivity of the zinc-alkyl derivatives greatly restricts the usability of this process.

Processes by means of which gallium alkyl compounds can be prepared by reaction of gallium halides with Grignard reagents are likewise known. However, the ethers used as solvent generally form stable adducts with the trialkylgallium compounds, and these are difficult to separate.

Furthermore, processes by means of which gallium alkyl compounds can be prepared from gallium trichloride and trialkylaluminium compounds as alkylated reagent are known. In these processes, the trialkylaluminium compound has to be used in an at least three-fold excess since only one alkyl group per aluminium is transferred to gallium, cf. equation (1):

$$GaCl_3 + 3R_3Al \rightarrow R_3Ga + 3R_2AlCl \qquad (1)$$

In addition, known processes usually proceed in a plurality of stages since starting materials or the product produced have to be purified or isolated in a complicated manner. Furthermore, only low yields of gallium alkyl compounds are frequently produced by the known processes.

The processes known from the prior art normally take place in the presence of organic solvents in order to ensure reaction of the components and a quantitative conversion. However, this can result in organic impurities in the gallium alkyl compounds. This has a significant adverse effect on the purity of the gallium alkyl compounds and thus their suitability as precursor for metal organic chemical vapour deposition processes (MOCVD). Thus, any impurities in the trialkylgallium would have a significant adverse effect on the optical and electrical properties of the semiconductor layers (e.g. GaAs) produced using an MOCVD process.

Industrially, trimethylgallium (TMG) is at present usually prepared from gallium trichloride and an excess of trimethylaluminium as methylating reagent. The use of trimethylaluminium has the disadvantage that it has hitherto had to be used in a large excess (see equation (1)).

Thus, US 2006/0075959 A1 describes a process for preparing trimethylgallium using trimethylaluminium.

EP 1489085 A1, too, discloses the preparation of TMG by reaction of gallium trichloride with trimethylaluminium in organic solvents such as mesitylene or dichlorobenzene.

The U.S. Pat. No. 7,166,734 describes, inter alia, the preparation of trimethylgallium from gallium trichloride and trimethylaluminium in the presence of stoichiometric amounts of triethylamine in toluene as solvent.

J. J. Eisch et al. describe a process for the preparation of triethylgallium and triisobutylgallium in hexane or pentane as a solvent with addition of potassium chloride. The potassium chloride (KCl) added forms a stable complex with the dialkylaluminium compound formed and thus prevents undesirable complexation of the gallium chloride by this compound. No salt melt is present. The products obtained generally contain solvent residues and are purified in a further step by redistillation over alkali metal fluorides (Eisch, J. J., *J. Am. Chem. Soc.*, 1962, 84, 3605-3610).

Gaines et al., too, refer to the preparation of trimethylgallium from trimethylaluminium and also a subsequent distillation over sodium fluoride followed by redistillation. The TMG yield is only about 63% (Gaines, D. F., Borlin, J., Fody, E. P., in: *Inorganic Syntheses*, 1974, 15, 203-207).

DE 1 158 977 describes the reaction of gallium trichloride with trialkylaluminium compounds or trialkylaluminium etherates. The trialkylgallium obtained is separated off by distillation and subsequently purified by rectification.

WO 00/37475 A1 discloses a continuous process for preparing TMG from trimethylaluminium and gallium trichloride in toluene.

Starowieyski et al. describe the preparation of TMG from gallium trichloride and dimethylaluminium chloride in the presence of excess sodium chloride (Starowieyski K. B. et al, *Applied Organometallic Chemistry*, 2000, 14, 10, 616-622). Here too, no salt melt is present.

DE 40 05 726 describes a process for preparing alkylgallium compounds from gallium-halogen compounds using alkylaluminium halides as alkylating agents and in the presence of alkaline earth metal chlorides or alkali metal chlorides as auxiliary bases. At the reaction temperature, the alkaline earth metal chlorides and alkali metal chlorides form a salt melt which is used as solvent. DE 40 05 726 refers to the use of alkylaluminium sesquichlorides ($R_3Al_2Cl_3$) for the preparation of the gallium alkyl compounds. The reaction is carried out without recirculation (separator) of the partially alkylated products, and the total yields of the fully alkylated products trimethylgallium and triethylgallium are from 10 to 48%.

It is therefore an object of the present invention to provide an improved process which makes an inexpensive preparation of trialkylgallium compounds possible. In particular, the process should be suitable for preparing trimethylgallium and triethylgallium. The process should be based on the use of industrially readily available starting materials and ensure high yields and a high efficiency in respect of the use of the expensive gallium starting materials and the alkylaluminium compounds.

The object of the present invention is achieved by the process according to the present claims. In particular, the object is achieved by an improved process which is, inter alia, characterized by the starting substances used (alkylaluminium compounds, auxiliary base) and the particular way of carrying out the reaction using a separator.

The terms which are frequently used in the present description are briefly defined below:

The direct yield ("crude yield") is the yield after step b) of the process of the invention.

The term "total yield" refers to the total yield of trialkylgallium obtained in the process.

The term "alkyl group utilization" is the ratio of the number of alkyl groups actually transferred to gallium to the number of alkyl groups introduced into the reaction.

The "total conversion based on gallium" is the sum of fully alkylated ($R_3Ga$) and partially alkylated ($R_cGaCl_d$) gallium compounds based on the amount of gallium-containing starting material used.

GENERAL DESCRIPTION OF THE INVENTION

The present invention relates to a process for preparing trialkylgallium compounds of the general formula $R_3Ga$ where R is a $C_1$-$C_5$-alkyl group, which comprises the steps:
a) reaction of gallium trichloride ($GaCl_3$) with an alkylaluminium compound of the type $R_aAlCl_b$ (where R is a $C_1$-$C_5$-alkyl group, a=1, 2 or 3, b=0, 1 or 2 and the sum a+b=3) in the presence of at least two alkali metal halides as auxiliary base;
b) heating of the reaction mixture to a temperature in the range from 120 to 250° C. with simultaneous separation of the trialkylgallium compound ($R_3Ga$) from the reaction mixture via a separator, where the separator is operated at a temperature which is more than 30° C. below, preferably more than 60° C. below, the boiling point of the most volatile partially alkylated product of the type $R_cGaCl_d$ (where R is a $C_1$-$C_5$-alkyl group, c, d=1 or 2 and c+d=3) formed in the reaction mixture.
The process can further comprise the step c):
c) heating of the reaction mixture to a temperature in the range from 165° C. to 350° C. and separation of the remaining trialkylgallium compound ($R_3Ga$) and the partially alkylated products ($R_cGaCl_d$) from the reaction mixture.
In this step c), the separator is not normally operated. However, a fine to high vacuum in the range from 1 to $10^{-3}$ mbar ($10^{-3}$ to $10^{-6}$ bar) can be applied to separate off the remaining partially alkylated compounds ($R_cGaCl_d$) still present in the reaction mixture. The vacuum makes it possible to use lower temperatures, so that the process can be carried out economically and inexpensively. This isolation of the remaining trialkylgallium compound ($R_3Ga$) and the partially alkylated products ($R_cGaCl_d$) can be carried out via a separate outlet from the reactor.

The process of the invention can further comprise the step d):
d) re-use of the partially alkylated products of the type $R_cGaCl_d$ obtained in step c) in the reaction mixture in step a) in order to produce further trialkylgallium compound.

In a particular embodiment, only the partially alkylated products ($R_cGaCl_d$) can be used in step a), with the addition of gallium trichloride ($GaCl_3$) being able to be omitted.

The process is based generally on the reaction of gallium trichloride ($GaCl_3$) with an alkylating reagent. The reaction takes place in a reactor which is advantageously operated batchwise.

However, a continuous process in which the starting materials (gallium trichloride and alkylaluminium compound) are introduced continually and the products are continuously separated off is also possible. Here, it is possible to use specific flow reactors and/or microreactors. The reactor types and process engineering modifications required for this are known to those skilled in the art.

The reaction is carried out in an inert gas atmosphere (argon or nitrogen). The reaction in step b) is preferably carried out under atmospheric pressure (=1±0.2 bar). However, depending on the boiling point of alkylgallium compound, a moderate vacuum (down to $10^{-3}$ bar) can also be applied.

DETAILED DESCRIPTION OF THE INVENTION

The present invention provides a process for preparing trialkylgallium compounds of the general formula $R_3Ga$. The radical R is generally an alkyl group having from 1 to 5 carbon atoms (i.e. a $C_1$-$C_5$-alkyl group). Examples are methyl, ethyl, n-propyl, isopropyl, n-butyl, isobutyl or tert-butyl groups. R is preferably a methyl or ethyl group.

As alkylated reagents, it is in principle possible to use all alkylaluminium compounds of the type $R_aAlCl_b$ (where R is a $C_1$-$C_5$-alkyl group, a=1, 2 or 3, b=0, 1 or 2 and the sum a+b=3). This formula encompasses the group of trialkylaluminium compounds ($R_3Al$), the group of dialkylaluminium compounds ($R_2AlCl$), the group of monoalkylaluminium compounds ($RAlCl_2$) or mixtures and combinations thereof. Examples are trimethylaluminium (TMA), dimethylaluminium chloride or triethylaluminium.

The alkylaluminium compound of the type $R_aAlCl_b$ is preferably selected from the group consisting of inexpensive alkylaluminium sesquichlorides ($R_3Al_2Cl_3$), which represent mixtures of the partially alkylated compounds $R_2AlCl$ and $RAlCl_2$. Examples are methylaluminium sesquichloride ($Me_3Al_2Cl_3$) and ethylaluminium sesquichloride ($Et_3Al_2Cl_3$). These starting materials have the advantage that they are formed as intermediates in the preparation of trimethylaluminium or triethylaluminium and require no complicated purification. Such products are commercially available from various manufacturers.

The use of these alkylated reagents thus makes a more inexpensive production process which is sparing of resources possible. It has surprisingly been found that when using, for example, methylaluminium sesquichloride as methylating reagent in the process of the invention, high direct yields of TMG can be achieved together with high alkyl group utilization and a very good total conversion based on gallium.

Reaction Step a)

In the process of the invention, the alkylaluminium compound can be used in a stochiometrically equivalent amount or in excess relative to the gallium trichloride. The term "equivalent" as used in the present patent application refers to the molar ratios based on the molar amounts of the starting materials relative to the stoichiometric ratios. In the preparation of the trialkylgallium compounds, preference is given to using from 1 to 5 equivalents, particularly preferably from 1 to 3 equivalents, of alkylaluminium compound per equivalent of gallium trichloride. In a particularly preferred embodiment, one equivalent of alkylaluminium sesquichloride is used per equivalent of gallium trichloride.

The reaction takes place in the presence of at least one auxiliary base. The auxiliary base comprises at least two alkali metal halides, preferably at least two alkali metal chlorides. Preference is also given to a mixture of the alkali metal chlorides sodium chloride (NaCl) and potassium chloride (KCl). Together with the aluminium-containing reaction products, in particular $AlCl_3$, these salts form a salt melt which is liquid at the reaction temperature. The use of additional organic solvents can therefore be dispensed with in the process of the invention.

The alkali metal chlorides used have to be water-free. For the purposes of the present invention, water-free means a water content of <10 ppm, more preferably <8 ppm and particularly preferably <5 ppm. A water content of >10 ppm can lead to secondary reactions and reduce the yield of trialkylgallium compound and impair its quality.

The auxiliary base particularly preferably comprises a mixture of potassium chloride and sodium chloride in which the molar ratio of sodium chloride to potassium chloride is in the range from 6:4 to 8:2 and preferably in the range from 6:3 to 8:3. In a particularly preferred embodiment, the molar ratio of NaCl to KCl is 7:3. The auxiliary base will hereinafter be referred to as "Na/KCl" for short.

The ratio of the equivalents of the auxiliary base Na/KCl used to the number of equivalents of the alkylating reagent used is preferably from 0.5:1 to 3:1, more preferably from 0.75:1 to 2.5:1. In a particularly preferred embodiment, the ratio of the equivalents of the auxiliary base Na/KCl used to the number of equivalents of the methylating reagent used is 2:1.

The auxiliary base is essentially used in such an amount that there is always one equivalent of auxiliary base present per equivalent of aluminium in the alkylaluminium compound. (Example: alkylating agent trimethylaluminium: 1 equivalent of Na/KCl per 1 equivalent of $Me_3Al$; alkylating agent $Me_3Al_2Cl_3$: 2 equivalents of Na/KCl per 1 equivalent of $Me_3Al_2Cl_3$). In the preferred embodiment of the process of the invention using NaCl and KCl as auxiliary base in the preferred ratio of sodium chloride to potassium chloride of 7:3, the eutectic salt melt $Na/KAlCl_4$ (ratio of $AlCl_3$:NaCl:KCl=50:35:15) is formed from the aluminium chlorides formed together with the auxiliary base when carrying out the reaction. Thus the salt melt becomes liquid at temperatures above 120° C. This enables the production of the alkylgallium compounds in an especially high direct yield in step b) of the process of the invention.

Since the reaction of gallium trichloride with the alkylaluminium compound proceeds exothermically, in a preferred embodiment one of the two starting materials is initially placed in the reactor together with the auxiliary base and the second starting material is subsequently introduced under temperature control into the initially charged mixture in order to achieve a safe reaction. The addition in step a) is carried out so that the reaction temperature is kept below the boiling point of the alkylaluminium compound used (for example, when using TMA, the reaction temperature should be kept below 120° C.).

In the simplest embodiment of the process, the solid starting materials are weighed into the reactor and the alkylaluminium compound which is liquid at room temperature is subsequently added in a controlled manner. This addition of the alkylaluminium compound to the mixture of gallium trichloride and auxiliary base is generally carried out via a dropping funnel. The addition of the alkylaluminium compound is preferably carried out while stirring the mixture of gallium trichloride and auxiliary base in order to ensure satisfactory mixing and a quantitative conversion.

In another variant of the process, a mixture comprising the alkylaluminium compound and auxiliary base is initially charged and the gallium trichloride is introduced under temperature control into this mixture. It is advantageous to melt the gallium trichloride (m.p. 78° C.) before the addition and introduce it in liquid form into the initially charged mixture, since introduction in liquid form is easier to controller from a reaction engineering point of view. In this variant, too, the addition is carried out so that the reaction temperature is kept below the boiling point of the alkylaluminium compound used (i.e. <120° C.).

In a further variant of the process, the salt melt can firstly be produced from auxiliary base and aluminium chloride before addition of the starting materials gallium trichloride and alkylaluminium compound.

The reaction time for step a) is basically dependent on the type of trialkylgallium compound to be prepared, on the batch size and on the process scale. On the laboratory scale, reaction times in the range from 0.5 to 4 hours are typical. For other batch sizes, suitable reaction times can easily be determined by experiment.

Reaction Step b)

After the reaction of the gallium trichloride with the alkylating reagent, the reaction mixture is heated to a temperature in the range from 120° C. to 250° C., preferably in the range from 125° C. to 200° C., in step b) in order to form and separate off the trialkylgallium compound ($R_3Ga$).

The separation from the reaction mixture is, in the process of the invention, carried out via a separator installed on the reactor, with partially alkylated products of the type $R_cGaCl_d$ (where c, d=1 or 2 and c+d=3) at the same time being recirculated to the reaction mixture by selection of the correct temperature profile on the separator As a result, these compounds are subjected to a further alkylation as per equation (4) described below and a high direct yield of trialkylgallium compound ($R_3Ga$) is thus achieved.

This separation is not quantitative; it preferably serves to recirculate the partially alkylated products to the reaction mixture in order to complete alkylation. In addition, the removal of the reaction product (trialkylgallium compound $R_3Ga$) from the reaction mixture shifts the equilibrium in the direction of the reaction products.

The process of the invention differs from the process previously disclosed in DE 40 05 726 for preparing alkylgallium compounds in a different way of carrying out the reaction and in particular in the use of a "separator". The use of this separator according to the invention surprisingly enables the desired trialkylgallium compound to be obtained in a significantly higher direct yield under comparable reaction conditions.

Thus, for example, in the case of trimethylgallium a direct yield of 68% is achieved by means of the process described here with the use of the separator and use of equivalent amounts of the starting materials (GaCl$_3$/Me$_3$Al$_2$Cl$_3$=1/1), while a trimethylgallium yield of only 25.6%, based on the gallium trichloride used, is obtained as reported in DE 40 05 726 (Example 4) with a comparable batch. When duplicating Example 4 of DE 40 05 726, the inventors found a yield of 21.3% trimethylgallium (ref to Comparative Example CE2).

As a result of this higher direct yield of trimethylgallium, the alkyl group utilization is also significantly increased compared to DE 40 05 726.

Figure 1:
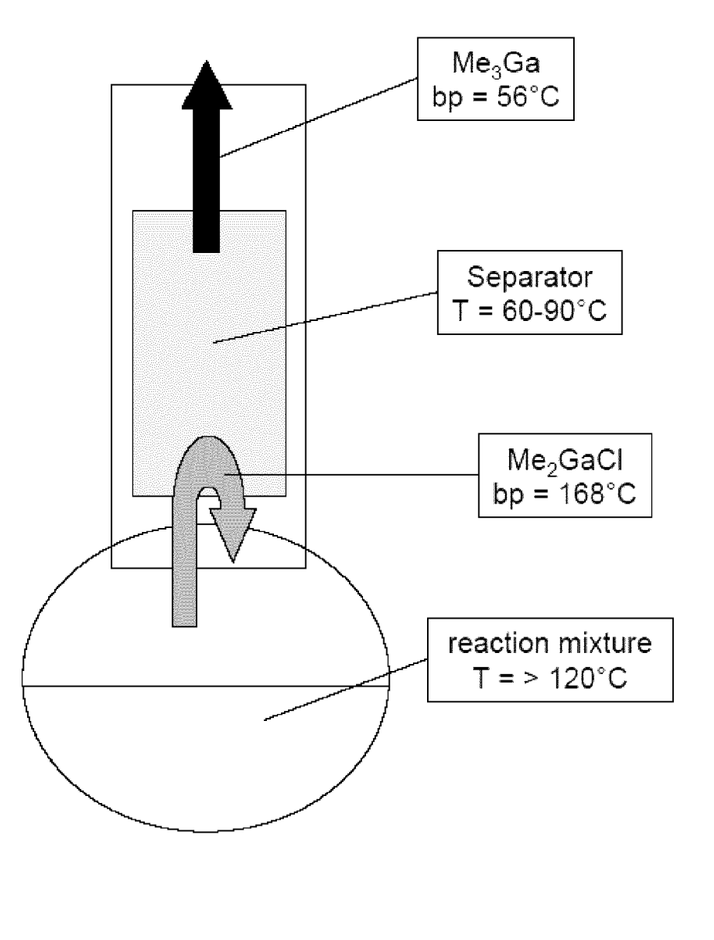

In FIG. 1 a schematic drawing of the process of the present invention is given. As an example, the preparation of Me$_3$Ga is illustrated.

To give a better understanding, the reaction steps proceeding during the process will be illustrated below for the example of the preparation of trimethylgallium by reaction of GaCl$_3$ with Me$_3$Al$_2$Cl$_3$. In principle, the following reaction occurs:

$$GaCl_3 + Me_3Al_2Cl_3 + 2Na/KCl \rightarrow Me_3Ga + 2Na/KAlCl_4 \qquad (2)$$

However, the reaction equation (2) indicates the way in which the reaction proceeds only imprecisely and incompletely. Thus, direct transfer of all methyl groups from aluminium to gallium cannot be observed, but instead only a partial alkylation in which dimethyl gallium chloride (Me$_2$GaCl) is formed; cf. equation (3), initially takes place at temperatures below 120° C.:

$$GaCl_3 + Me_3Al_2Cl_3 + 2Na/KCl \rightarrow Me_2GaCl + Na/KMeAlCl_3 + Na/KAlCl_4 \qquad (3)$$

The occurrence of the monomethylated species methylgallium dichloride (MeGaCl$_2$) can, on the other hand, generally not be observed. When the reaction melt is heated to temperatures above 120° C., preferably above 125° C., the partially alkylated species is then alkylated further by the alkyl groups still present in the reaction melt to form trimethylgallium; cf. equation (4):

$$Me_2GaCl + Na/KMeAlCl_3 \rightarrow Me_3Ga + Na/KAlCl_4 \qquad (4)$$

Without this heating of the reaction mixture, the second alkylation step does not take place and only Me$_2$GaCl can be isolated as product immediately after the addition of GaCl$_3$ to the Me$_3$Al$_2$Cl$_3$.

During heating, too, mainly dimethylgallium chloride and only small amounts of the trimethylgallium being formed consequently occur in the reaction melt. As a result of the high temperatures prevailing during heating, the trimethylgallium formed is immediately distilled off from the reaction melt.

However, since the formation and liberation of trimethylgallium takes place only in a temperature range in which the boiling range of the major partially alkylated species dimethylgallium chloride (Me$_2$GaCl, b.p. 167-168° C.) is likewise located, a mixture of completely and partially alkylated products will always be isolated in the process described in DE 40 05 726.

Only the use of a separator operated in a suitable temperature range as a function of the product makes it possible to isolate the desired trialkylgallium compound without simultaneous separation of the partially alkylated species from the reaction mixture. As a result of the recirculation (effected by means of the separator) of the partially alkylated compound into the reaction mixture, this is advantageously subjected to a further alkylation as per equation (4), so that the achievable yields of trialkylgallium compound can be significantly increased compared to the literature process by the use according to the invention of the separator.

A person skilled in the art will value the fact that the utilization of the alkyl equivalents used is also significantly increased in this way. Thus, when trimethylaluminium is used for the preparation of trimethylgallium from gallium trichloride by processes known in the literature, only one of three methyl groups are transferred from aluminium to gallium, while in the process of the invention virtually all methyl groups can be transferred from aluminium. The process of the invention thus makes it possible to save expensive alkylating reagent and therefore provides a significant improvement over the conventional process as described in DE 40 05 726. Compared to the processes known from the literature which employ TMA as alkylating reagent, too, a considerable improvement is achieved.

On the laboratory scale, the process can be carried out in a four-neck flask provided with stirrer, dropping funnel, a separator and a further outlet. Corresponding pilot plants can optionally be modified in process engineering terms and corrosion-resistant materials should be used in them. Industrial production plants can also be designed for continuous operation by means of appropriate modifications.

The trialkylgallium compound formed in reaction step a) is isolated from the residual mixture remaining in the reactor. The isolation is preferably carried out by distillation using a separator which in principle represents a heated separation element which allows separation of individual components on the basis of their different boiling ranges. For example, a heated packed column or a heated reflux condenser can be used on the laboratory scale. On the pilot plant scale or in industrial production, appropriately dimensioned separation elements in their industrial embodiments should be used.

The separator is, according to the invention, operated at a temperature which is more than 30° C. below, preferably more than 60° C. below, the boiling point of the most volatile partially alkylated gallium compound R$_c$GaCl$_d$ (where c, d=1 or 2 and c+d=3) formed in the reaction mixture.

Furthermore, the separator is generally heated to a temperature which is from 5 to 40° C. above, preferably from 10 to 25° C. above, the boiling point of the trialkylgallium compound R$_3$Ga formed in the reaction mixture.

In the case of trimethylgallium (TMG, b.p. 56° C.), the separator is heated at atmospheric pressure (=1±0.2 bar) to a temperature in the range from 60 to 90° C., preferably to a temperature in the range from 70 to 80° C. It is particularly preferably operated at about 70° C. This temperature is 14° C. above the boiling point of TMG and 98° C. below the boiling point of dimethylgallium chloride (b.p. 167-168° C.). The isolation by distillation of TMG by means of the separator is preferably carried out under atmospheric pressure.

In the case of triethylgallium (TEG, b.p. 143° C.), the separator is heated to a temperature in the range from 150 to 180° C., preferably to a temperature in the range from 155 to 170° C., when carrying out the process at atmospheric pressure (=1±0.2 bar). However, for the preparation of triethylgallium, the process of the invention is preferably carried out under reduced pressure in step b) and the temperature of the separator is adapted to the reduced boiling point of the partially alkylated product. Thus, the boiling point of diethylgallium chloride is 60-62° C. (at 3 mbar).

For the preparation of TEG, a separator temperature in the range from 100 to 160° C., preferably in the range from 120 to 150° C., at a reduced pressure in the range of up to 1 mbar ($10^{-3}$ bar) has been found to be useful in the process of the invention.

In the case of the preparation of tri(tert-butyl)gallium (b.p. 69-73° C. at 5 mbar), step b) is likewise preferably carried out under a reduced pressure in the range up to 1 mbar ($10^{-3}$ bar).

Reaction Step c)

After the isolation of the trialkylgallium compound in step b) of the process of the invention is concluded, the reaction mixture can, in step c), be heated further to a temperature in the range from 165° C. to 350° C., preferably to a temperature in the range from 180° C. to 250° C. Here, the remaining trialkylgallium compound ($R_3Ga$) and the partially alkylated products $R_cGaCl_d$ are separated off from the reaction mixture. This isolation is carried out by distillation, preferably with application of a reduced pressure. Preference is given to selecting a fine to high vacuum in the range from 1 to $10^{-3}$ mbar. This makes virtually complete removal of all volatile compounds from the reaction mixture possible and the purely inorganic salt melt formed from the auxiliary base and the aluminium chloride formed in the reaction remains as residue.

The reduced pressure allows the use of comparatively low temperatures, so that the process can be carried out economically and inexpensively. The isolation of the mixture of trialkylgallium compound ($R_3Ga$) and partially alkylated product $R_cGaCl_d$ is preferably carried out via a separate outlet on the reactor.

Reaction Step d)

In a preferred variant of the process, the partially alkylated products ($R_cGaCl_d$) isolated by the separation from the reaction mixture in step c), which are generally present in a mixture with small amounts of trialkylgallium compound ($R_3Ga$), are, in step d), re-used in a further batch. Here, the gallium trichloride ($GaCl_3$) in process step a) can be completely or partly replaced by partially alkylated products of the type $R_cGaCl_d$.

This optional recycling of the expensive gallium compound makes the process of the invention particularly economical. Furthermore, for example in the case of TMG, the gallium utilization and the total TMG yield can be increased further.

According to the invention, a salt melt which is liquid at the reaction temperature remains as residual mixture after carrying out steps a) to d). In general, no relatively large amounts of pyrophoric alkyl metal compounds remain in the residual mixture. This has the advantage that complicated and costly disposal is dispensed with. In particular, the residual mixture comprises salt-like compounds of the composition Na/K [$AlCl_4$], Na/K[$MeAlCl_3$] and mixtures thereof.

The individual reaction steps a), b) and optionally c) and d) of the process of the invention can also, if required, be carried out in a plurality of substeps independently in respect of time (for example with hold times between the individual steps) in the order described.

SUMMARY

The invention relates to a process for preparing trialkylgallium compounds of the general formula $R_3Ga$. The process is based on the reaction of gallium trichloride ($GaCl_3$), optionally in a mixture with partially alkylated products, with an alkylaluminium compound of the type $R_aAlCl_b$ (where R=$C_1$-$C_5$-alkyl, a=1, 2 or 3, b=0, 1 or 2 and a+b=3) in the presence of at least two alkali metal halides (e.g. NaCl and KCl) as auxiliary base. Preference is given to using alkylaluminium sesquichloride ($R_3Al_2Cl_3$) or trialkylaluminium ($R_3Al$). The reaction mixture is heated to a temperature in the range from 120° C. to 250° C. and the trialkylgallium compound formed is separated off via a separator which is operated at a temperature which is more than 30° C. below the boiling point of the most volatile partially alkylated product.

Complete alkylation is achieved here and partially alkylated products are recirculated to the reaction mixture. In a further step, the reaction mixture can be heated to a maximum of 350° C. and the remaining fully alkylated and partially alkylated products can be separated off.

The process gives a high yield of trialkylgallium compound and displays high gallium utilization; the products are used as precursors for MOCVD processes.

Compared to the conventional processes as described in DE 40 05 726, very high direct yields in the range from 60 to 90% can be achieved in the preparation of trialkylgallium compounds (in particular TMG) by means of the process of the invention. For the purposes of the present invention, the direct yield ("crude yield") is the yield after step b) of the process. The trialkylgallium compounds present in the direct yield generally still contain from 0.1 to 1 wt.-% of dialkylated products (measured by means of $^1$H-NMR).

To calculate the total yield, any trialkylgallium compounds isolated in step c) of the process are included. In this way, total yields of up to 99% (in the case of TMG, based on Ga) are obtained. To calculate the gallium utilization, the yields of trialkylgallium compounds and partially alkylated compounds obtained are added together.

The trialkylgallium compounds obtained from the process of the invention are generally subjected to a fine purification in a subsequent step in order to achieve the 6N purity (corresponding to 99.9999% purity based on gallium) required for use in the MOCVD industry. This is generally a rectification and/or a distillation, optionally in a plurality of steps. Suitable further purification processes are described in the literature.

The trialkylgallium compounds, in particular trimethylgallium (TMG), triethylgallium (TEG) or tri-tert-butylgallium, are used, e.g., as metal organic precursors for metal organic chemical vapour deposition (MOCVD), for example for producing semiconductor layers composed of GaAs. The semiconductor layers (III/V semiconductors, etc.) ultimately produced therefrom have a variety of industrial uses.

The invention is now explained in more detail by the following examples, which are considered illustrative, but do not limit the scope of the invention and the resulting claims.

EXAMPLES

General

The alkylmetal compounds prepared and the alkylaluminium compounds used in the synthesis are pyrophoric. All work is therefore carried out with rigorous exclusion of air and moisture and a protective gas (argon, nitrogen).

Example 1

Preparation of Trimethylgallium (TMG)

117.3 g (0.57 mol, 1 equivalent) of methylaluminium sesquichloride ($Me_3Al_2Cl_3$, Chemtura Organometallics GmbH, Bergkamen, DE), 46.6 g (0.80 mol, 1.4 equivalents) of dry NaCl (Merck, water content <5 ppm) and 25.5 g (0.34 mol, 0.6 equivalent) of dry KCl (Merck, water content <5 ppm) are placed under inert gas (argon, purity 6.0) in a 500 ml four-neck flask provided with stirrer, heatable dropping funnel and a separator maintained at 70° C. and also a further outlet.

While stirring, 100.0 g (0.57 mol) of molten $GaCl_3$ (high-purity, MCP Group, Tilly, BE) are added from a dropping funnel heated to 90° C. in such a way that the temperature in the reaction mixture does not exceed 120° C. The ratio of equivalents of $GaCl_3$ to $Me_3Al_2Cl_3$ is 1:1.

During the subsequent heating up, Me$_3$Ga can be isolated above about 155° C. The end point of the isolation of the product via the separator is identified by means of a sharp increase in the internal temperature of the reaction to >190° C. 45.4 g of Me$_3$Ga are obtained, corresponding to a direct yield of 69.6%. The remaining gallium-containing compounds are subsequently removed from the reaction mixture via a second outlet with application of reduced pressure (to 10$^{-3}$ mbar, oil pump) (22.4 g, mixture of Me$_3$Ga and Me$_2$GaCl).

The total yield is 75.1% of Me$_3$Ga. Taking into account 24.7% of Me$_2$GaCl, the total conversion based on Ga is thus 99.8%. The crude Me$_3$Ga isolated as direct yield contains 0.3 wt.-% of Me$_2$GaCl as impurity (measured by means of $^1$H-NMR). The mixture of Me$_3$Ga and Me$_2$GaCl is re-used in other batches (cf. Example 2).

Example 2

Preparation of TMG (with Re-Use)

183.1 g (1.04 mol) of GaCl$_3$, 92.9 g (1.59 mol) of dry NaCl, 50.8 g (0.68 mol) of dry KCl and also 40.4 g (0.3 mol) of Me$_2$GaCl and 5.5 g (0.05 mol) of Me$_3$Ga (isolated mixture from previous experiment) are placed under inert gas in a 500 ml four-neck flask provided with stirrer, dropping funnel and a separator maintained at 70° C. and also a further outlet.

While stirring 233 g (1.14 mol) of Me$_3$Al$_2$Cl$_3$ are added in such a way that the temperature in the reaction mixture does not exceed 120° C. During subsequent heating up, Me$_3$Ga is isolated (99.3 g, corresponding to a direct yield of 61.7%).

When the reaction temperature reaches 190° C., the isolation of the product by the separator is stopped and the remaining gallium-containing compounds (residue) are isolated from the residual mixture via the second outlet with application of a reduced pressure (70.0 g, mixture of Me$_3$Ga and Me$_2$GaCl).

The total yield is 64.0% of Me$_3$Ga. Taking into account 35.8% of Me$_2$GaCl, the total conversion (based on Ga) is 99.8%.

The isolated crude Me$_3$Ga from the direct yield contains 0.8 wt.-% of Me$_2$GaCl (measured by $^1$H-NMR). The isolated mixture of Me$_3$Ga and Me$_2$GaCl is recirculated in a further pass in a manner analogous to the procedure described.

Example 3

Preparation of TMG (Ratio of Equivalents=1:3)

45.0 g (0.26 mol) of GaCl$_3$, 62.7 g (1.07 mol, 4.2 equivalents) of dry NaCl and 34.3 g (0.46 mol, 1.8 equivalents) of dry KCl are placed under argon in a 500 ml four-neck flask provided with stirrer, dropping funnel and a separator maintained at 70° C.

While stirring, 162.8 g (0.79 mol, 3 equivalents) of Me$_3$Al$_2$Cl$_3$ are added in such a way that the temperature in the reaction mixture does not exceed 120° C. During subsequent heating up, Me$_3$Ga is isolated (26.6 g; corresponding a direct yield of 88% of Me$_3$Ga).

After the isolation of product by the separator is complete, the remaining gallium-containing compounds are removed from the residual mixture via a second outlet with application of a reduced pressure (6.9 g).

In total, 99.0% of Me$_3$Ga and 0.9% of Me$_2$GaCl are isolated, and the total conversion (based on Ga) is 99.9%. The isolated crude Me$_3$Ga contains 0.7 wt.-% of Me$_2$GaCl and 1.4 wt.-% of Me$_2$AlCl (measured by means of $^1$H-NMR).

Example 4

Preparation of Triethylgallium (TEG)

68.9 g (0.39 mol) of GaCl$_3$, 32.0 g (0.55 mol, 1.4 equivalents) of dry NaCl and 17.5 g (0.23 mol, 0.6 equivalent) of dry KCl are placed under argon in a 500 ml four-neck flask provided with stirrer, dropping funnel and a separator maintained at 130° C.

While stirring, 120.2 g (0.47 mol, 1.2 equivalents) of ethylaluminium sesquichloride (Et$_3$Al$_2$Cl$_3$) are added in such a way that the temperature in the reaction mixture does not exceed 120° C. The reaction mixture is subsequently heated while applying a reduced pressure of 300 mbar, and Et$_3$Ga is thus isolated (46.6 g; direct yield 75.9%). After the isolation of the product via the separator is complete, the remaining gallium-containing compounds are removed from the reaction mixture via a second outlet under a high vacuum (to 10$^{-3}$ mbar) (14.6 g, mixture of Et$_3$Ga and Et$_2$GaCl).

In total, 80.9% of Et$_3$Ga and 19% of Et$_2$GaCl are isolated, and the total yield (based on Ga) is 99.9%. The isolated crude Et$_3$Ga contains 2.6 wt.-% of Et$_2$GaCl (measured by means of $^1$H-NMR).

Example 5

Preparation of TMG (Ratio of Equivalents=1:1.5)

170 g (0.97 mol) of GaCl$_3$, 118.5 g (2.03 mol, 2.1 equivalents) of dry NaCl and 64.9 g (0.87 mol, 0.9 equivalents) of dry KCl are placed under argon in a 500 ml four-neck flask provided with stirrer, dropping funnel and a separator maintained at 70° C.

While stirring, 289.1 g (1.45 mol, 1.5 equivalents) of Me$_3$Al$_2$Cl$_3$ are added in such a way that the temperature in the reaction mixture does not exceed 120° C. During subsequent heating up, Me$_3$Ga is isolated (97.8 g; direct yield 87%). The remaining gallium-containing compounds are subsequently removed from the residual mixture via a second outlet with application of a reduced pressure (14.8 g, mixture of Me$_3$Ga and Me$_2$GaCl).

In total, 95.6% of Me$_3$Ga and 4% of Me$_2$GaCl are isolated, corresponding to a Ga utilization of 99.6%. The isolated crude Me$_3$Ga contains <0.7 wt.-% of Me$_2$GaCl as impurity ($^1$H-NMR).

Example 6

Preparation of TMG (Use of Me$_3$Al as Methylating Reagent)

150 g (0.85 mol) of GaCl$_3$, 34.9 g (0.60 mol, 0.7 equivalent) of dry NaCl and 19.1 g (0.26 mol, 0.3 equivalent) of dry KCl are placed under argon in a 500 ml four-neck flask provided with stirrer, dropping funnel and a separator maintained at 70° C.

While stirring, 62.9 g (0.85 mol, 1 equivalent) of Me$_3$Al (Sigma Aldrich) are added in such a way that the temperature in the reaction mixture does not exceed 120° C. During subsequent heating up, Me$_3$Ga is isolated (68.3 g; direct yield 69.6%). The residual gallium-containing compounds are subsequently removed from the residual mixture via a second outlet with application of a reduced pressure (34.5 g, mixture of Me$_3$Ga and Me$_2$GaCl).

In total, 71.3% of $Me_3Ga$ and 25.6% of $Me_2GaCl$, corresponding to a Ga utilization of 96.9%, are isolated. The isolated crude $Me_3Ga$ contains <0.2 wt.-% of $Me_2GaCl$ as impurity ($^1H$-NMR).

Comparative Example CE1

Preparation of TMG Without Use of the Separator 20.0 g (0.11 mol) of $GaCl_3$, 9.49 g (0.16 mmol, 1.4 equivalents) of dry NaCl and 5.16 g (0.07 mol, 0.6 equivalent) of dry KCl are placed under argon in a 100 ml three-neck flask provided with stirrer and dropping funnel. While stirring, 23.1 g (0.11 mol, 1 equivalent) of $Me_3Al_2Cl_3$ are added in such a way that the temperature in the reaction mixture does not exceed 120° C. The ratio of equivalents of $GaCl_3$ to $Me_3Al_2Cl_3$ is 1:1 (cf. Example 1).

The reaction mixture is subsequently heated to 180° C., and 11.28 g of a product mixture of $Me_3Ga$ and $Me_2GaCl$ are distilled off. After 2 hours at 180° C., the residual gallium-containing compounds are removed from the reaction mixture with application of a reduced pressure (to $10^{-3}$ mbar, oil pump) (2.16 g, $Me_2GaCl$). The product mixture obtained as first fraction is separated by cold distillation in a high vacuum. 9.61 g of $Me_3Ga$ and 1.67 g of $Me_2GaCl$ are obtained. The $Me_3Ga$ separated off still contains 9.8 wt.-% of $Me_2GaCl$ (measured by means of $^1H$-NMR). Taking into account the $Me_2GaCl$ impurities still present, the total yield is 65.1% of $Me_3Ga$. Taking into account 32.3% of $Me_2GaCl$, the total conversion based on Ga is thus 97.4%.

Comparative Example CE2

TMG, According to DE 40 05 726, Example 4

A 500 ml 4-neck flask equipped with stirrer, thermocouple and dropping funnel is charged with $GaCl_3$ (50.0 g, 0.28 mol) and methylaluminum sesquichloride (58.3 g, 0.28 mol, 1 equivalent) is added dropwise via the dropping funnel. After the reaction mixture has cooled to room temperature the flask is transferred to a glovebox and dry NaCl (23.2 g, 0.40 mol, 1.4 equivalents) and dry KCl (12.7 g, 0.17 mol, 0.6 equivalent) are added. The dropping funnel is replaced with a CLAISEN head with attached cold-trap. The apparatus is taken out of the glovebox and the reaction mixture is slowly heated under constant stirring to 350° C. At a temperature between 100 and 120° C. the reaction mixture becomes liquid; between 155 and 160° C. a clear liquid starts to distill off and is collected in an ice-cooled cold-trap. The collected product, at room temperature partially solid, overall 36.9 g, is identified by means of NMR as a mixture of $Me_3Ga$ and $Me_2GaCl$, containing 21.3% $Me_3Ga$ and 78.7% $Me_2GaCl$.

The invention claimed is:

1. Process for preparing trialkylgallium compounds of the general formula $R_3Ga$ where R is a $C_1$-$C_5$-alkyl group, which comprises the steps:
a) reaction of gallium trichloride ($GaCl_3$) with an alkylaluminium compound of the type $R_aAlCl_b$ (where R is a $C_1$-$C_5$-alkyl group, a=1, 2 or 3, b=0, 1 or 2 and the sum a+b=3) in the presence of at least two alkali metal halides as auxiliary base;
b) heating of the reaction mixture to a temperature in the range from 120 to 250° C. with simultaneous separation of the trialkylgallium compound ($R_3Ga$) formed from the reaction mixture via a separator, where the separator is operated at a temperature which is more than 30° C. below the boiling point of the most volatile partially alkylated product of the type $R_cGaCl_d$ (where R is a $C_1$-$C_5$-alkyl group, c, d=1 or 2 and c+d=3) formed in the reaction mixture.

2. Process according to claim 1, which further comprises the step
c) heating of the reaction mixture to a temperature in the range from 165° C. to 350° C. and separation of the remaining trialkylgallium compound ($R_3Ga$) and the partially alkylated products ($R_cGaCl_d$) from the reaction mixture.

3. Process according to claim 2, which further comprises the step
d) re-use of the partially alkylated products of the type $R_cGaCl_d$ obtained in step c) in the reaction mixture in step a).

4. Process according to claim 1, wherein, in step a), the gallium trichloride ($GaCl_3$) is completely or partly replaced by re-used partially alkylated products of the type $R_cGaCl_d$.

5. Process according to claim 1, wherein the alkylaluminium compound of the type $R_aAlCl_b$ is selected from the group consisting of trialkylaluminium compounds ($R_3Al$), dialkylaluminium compounds ($R_2AlCl$), monoalkylaluminium compounds ($RAlCl_2$)) and mixtures thereof.

6. Process according to claim 1, wherein the alkylaluminium compound of the type $R_aAlCl_b$ is selected from the group consisting of alkylaluminium sesquichlorides.

7. Process according to claim 1, which further comprises the fine purification of the trialkylgallium compound in a subsequent step.

8. Process according to claim 1, where R is a methyl, ethyl, n-propyl, isopropyl, n-butyl, isobutyl or tert-butyl group.

9. Process according to claim 1, wherein the separator in step b) is operated at atmospheric pressure (=1±0.2 bar) or at a reduced pressure to $10^{-3}$.

10. Process according to claim 2, wherein the remaining trialkylgallium compound ($R_3Ga$) and the partially alkylated products from the reaction mixture in step c) is carried out under a reduced pressure in the range from $10^{-3}$ to $10^{-6}$ bar (from 1 to $10^{-3}$ mbar).

11. Process according to claim 1, wherein methylaluminium sesquichloride [$(CH_3)_3Al_2Cl_3$], ethylaluminium sesquichloride [$(C_2H_5)_3Al_2Cl_3$)], trimethylaluminium [$(CH_3)_3Al$], triethylalurninium [$(C_2H_5)_3Al$] or tri-tert-butylaluminium [$(CH_3)_3C)_3Al$] is used as alkylaluminium compound.

12. Process according to claim 1, wherein a heatable separation element or a heatable packed column is used as separator.

13. Process according to claim 1, wherein the separator is operated at a temperature which is from 5 to 40° C. above the boiling point of the trialkylgallium compound $R_3Ga$ formed in the reaction mixture.

14. Process according to claim 1, wherein the trialkylgallium compound is trimethylgallium and the separator is operated at a temperature in the range from 60 to 90° C.

15. Process according to claim 1, wherein the trialkylgallium compound is triethylgallium and the separator is operated under reduced pressure in the range of up to 1 mbar ($10^{-3}$ bar) at a temperature in the range from 100 to 160° C.

16. Process according to claim 1, wherein at least two alkali metal chlorides are is are used as auxiliary base in step a).

17. Process according to claim 1, wherein the molar ratio of NaCl to KCl in the auxiliary base is in the range from 6:3 to 8:3.

18. Process according to claim 1, wherein a salt melt which is liquid at the reaction temperature is formed by the auxiliary base in combination with the aluminium-containing reaction product in step b).

19. Process according to claim 1, wherein, in step a), the ratio of the equivalents of auxiliary base used to number of equivalents of alkylaluminium compound used is in the range from 0.5:1 to 3:1.

20. Process according to claim 1, wherein from 1 to 5 equivalents of alkylaluminium compound are used per equivalent of gallium trichloride in step a).

21. Process according to claim 1, wherein at least the steps a) and b) are carried out continuously in suitable reactors.

22. Process according to claim 1, wherein in step h) the partially alkylated products of the type $R_cGaCl_d$ (where R is a $C_1$-$C_5$-alkyl group, c, d=1 or 2 and c+d=3) are recirculated in the reaction mixture by means of the separator.

23. Process according to claim 1, wherein the trialkylgallium compound ($R_3Ga$) is obtained in direct yields in the range from 60 to 90%.

24. The process of claim 1, wherein the separator is operated at a temperature which is more than 60° C. below the boiling point of the most volatile partially alkylated product of the type $R_cGaCl_d$ (where R is a $C_1$-$C_5$-alkyl group, c, d=1 or 2 and c+d=3) formed in the reaction mixture.

25. The process of claim 6, wherein the alkylaluminium sesquichlorides are trialkylaluminium sesquichlorides ($R_3Al_2Cl_3$, i.e. mixtures of $R_2AlCl$ and $RAlCl_2$).

26. The process of claim 8, wherein R is a methyl or ethyl group.

27. The process of claim 13, wherein the separator is operated at a temperature which is from 10 to 25° C. above the boiling point of the trialkylgallium compound $R_3Ga$ formed in the reaction mixture.

28. The process of claim 14, wherein the separator is operated at a temperature in the range from 70 to 80° C.

29. The process of claim 15, wherein the separator is operated under reduced pressure in the range of up to 1 mbar ($10^{-3}$ bar) at a temperature in the range from 100 to 150° C.

30. The process of claim 16, wherein a mixture of sodium chloride (NaCl) and potassium chloride (KCl) is used as auxiliary base in step a).

31. The process of claim 19, wherein, in step a), the ratio of the equivalents of auxiliary base used to number of equivalents of alkylaluminium compound used is in the range from 0.75:1 to 2.5:1.

32. The process of claim 20, wherein from 1 to 3 equivalents of alkylaluminium compound are used per equivalent of gallium trichloride in step a).

33. The process of claim 7, wherein the fine purification comprises rectification, distillation, or combinations thereof.

34. The process of claim 17, wherein the molar ratio of NaCl to KCl in the auxiliary base is 7:3.

* * * * *